United States Patent
Maul et al.

(10) Patent No.: US 6,703,404 B2
(45) Date of Patent: Mar. 9, 2004

(54) TERT-BUTYL-(7-METHYL-IMIDAZOL[1,2-A]PYRIDIN-3-YL)-AMINE DERIVATIVES

(75) Inventors: Corinna Maul, Aachen (DE); Bernd Sundermann, Aachen (DE); Hagen-Heinrich Hennies, Simmerath (DE); Johannes Schneider, Stolberg (DE); Matthias Gerlach, Brachttal (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/117,339

(22) Filed: Apr. 8, 2002

(65) Prior Publication Data

US 2003/0022914 A1 Jan. 30, 2003

Related U.S. Application Data

(63) Continuation of application No. PCT/EP00/09791, filed on Oct. 6, 2000.

(30) Foreign Application Priority Data

Oct. 8, 1999 (DE) .......................... 199 48 434

(51) Int. Cl.[7] .................. A61K 31/437; C07D 471/04; A61P 25/00; A61P 29/00
(52) U.S. Cl. ........................ 514/300; 546/121
(58) Field of Search .................. 546/121; 514/300

(56) References Cited

U.S. PATENT DOCUMENTS

| 5,908,842 A | * | 6/1999 | Guthikonda et al. ... 514/253.01 |
| 6,379,649 B1 | * | 4/2002 | Katsifis et al. ............. 424/1.85 |

OTHER PUBLICATIONS

Adrian J. Hobbss, et al., "Inhibition of Nitric Oxide Synthase as a Potential Therapeutic Target" Annu. Rev. Pharmacy, vol. 39, 1999.

"Nitric oxide: from basic research to clinical applications" DDT, vol. 4, No. 2, Feb. 1999.

P. E. Chabrier, et al., "Nitric oxide synthases: targets for therapeutic strategies in neurological diseases" CMLS, Cell Mol. Life Science, vol. 55, 1999.

Lars L. Thomsen, et al., "Nitric Oxide Theory of Migraine" Clinical Neuroscience, vol. 5, 1998.

L. H. Lassen, et al., "Nitric oxide synthase inhibition in migraine" The Lancet, vol. 349, Feb. 8, 1997.

Ferid Murad, et al., "Discovery of Some of the Biological Effects of Nitric Oxide and Its Role in Cell Signaling (Nobel Lecture)" Ange. Chem. Int. Ed., vol. 38, 1999.

Louis J. Ignarro, "Stickstoffmonoxide: ein einzigarties endogenes Signalmolekuel in der Gerfaebiologie (Nobel–Vortrag)" Angew, Chemistry, vol. 111, 1999.

* cited by examiner

Primary Examiner—Evelyn Mei Haung
(74) Attorney, Agent, or Firm—Crowell & Moring LLP

(57) ABSTRACT

A Tert.-butyl-(7-methyl-imidazo[1,2-a]pyridin-3-yl)-amine derivatives of Formula I:

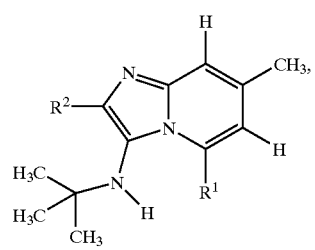

wherein the pharmaceutically acceptable salts, methods of making and method of use, in particular for the treatment of migraine.

21 Claims, No Drawings

TERT-BUTYL-(7-METHYL-IMIDAZOL [1,2-A]PYRIDIN-3-YL)-AMINE DERIVATIVES

CROSS REFERENCE TO RELATED APPLICATIONS

The present application is a continuation of international patent application no. PCT/EP00/09791, filed Oct. 6, 2000, designating the United States of America, the entire disclosure of which is incorporated herein by reference. Priority is claimed based on Federal Republic of Germany patent application no. 199 48 434.1, filed Oct. 8, 1999.

BACKGROUND OF THE INVENTION

This invention relates to tert.-butyl-(7-methyl-imidazo[1,2-a]pyridin-3-yl)-amine derivatives, to a method of producing them, to drugs which contain these compounds, to methods for inhibiting NO synthase and for the treatment of migraine, etc., using the tert.-butyl-(7-methyl-imidazo[1,2-a]pyridin-3-yl)-amine derivatives according to the invention and also relates to pharmaceutical compositions which contain tert.-butyl(7-methyl-imidazo[1,2-a]pyridin-3-yl)-amine derivatives.

Nitrogen monoxide (NO) regulates numerous physiological processes, including neurotransmission, the relaxation and proliferation of smooth musculature, the adhesion and aggregation of thrombocytes, as well as tissue damage and inflammation, amongst others. Due to its multiplicity of signal functions, NO is associated with a whole series of diseases (see L. J. Ignarro, Angew. Chem. (1999). 111, 2002–2013 and F. Murad. Angew. Chem. Int. Ed. (1999), 111, 1976–1989, for example). The enzyme which is responsible for the physiological formation of NO, namely NO synthase (NOS), thus plays an important part in the effect of therapy on these diseases. Three different isoforms of NO synthase, namely the two constituent nNOS and eNOS, as well as the inducable form INOS, have hitherto been identified (A. J. Hobbs. A. Higgs, 5. Moncada. Annu. Rev. Pharmacol. Toxicol. (1999), 39, 191–220; I. C. Green, P. -E. Chabrier, DDT(1999), 4, 47–49; P. -E. Chabrier et al. Cell. Mol. Life Sci. (1999), 55, 1029–1035).

The inhibition of NO synthase opens up new approaches to therapy for various diseases which are associated with NO (A. J. Hobbs et al. Annu. Rev.Pharmacol Toxicol. (1999), 39, 191–220; I. C. Green. P. -E. Chabrier, DDT (1999), 4, 47–49: P. -E. Chabrier et al., Cell. Mol. Life Sci. (1999), 55, 1029–1035), such as migraine (L. L. Thomsen. J. Olesen. Clinical Neuroscience (1998), 5, 28–33; L. H. Lassen et al., The Lancet (1997), 349, 401–402), septic shock, neurodegenerative diseases such as multiple sclerosis, Parkinson's disease, Alzheimer's disease or Huntington's disease, inflammation, pain due to inflammation, cerebral ischaemia, diabetes, meningitis and arteriosclerosis. Furthermore, NOS inhibition can also have an effect on the healing of wounds, on tumours and on angiogenesis, as well as giving rise to non-specific immunity in relation to microorganisms (A. J. Hobbs et al. Annu. Rev. Pharmacol. Toxicol. (1999), 39, 191–220).

Apart from $N^G$-monomethyl-L-arginine (L-NMMA) and $N^W$-nitro-L-arginine methylester (L-NAME)—i.e. analogues of L-arginine from which NO and citrulline are formed in vivo with the participation of NOS, the active ingredients known hitherto which inhibit NO synthase are S-methyl-L-citrullin, aminoguanidine, S-methylisourea, 7-nitromidazole and 2-mercaptoethylguanidine, etc., (A. J. Hobbs et al., Annu. Rev. Pharmacol. Toxicol. (1999), 39, 191–220).

In contrast, the underlying object of the present invention was to provide new, effective NOS inhibitors.

SUMMARY AND DETAILED DESCRIPTION OF THE INVENTION

It has surprisingly been found that 3-tert.-butyl-amino-substituted imidazo[1,2-a]pyridines of general structure I

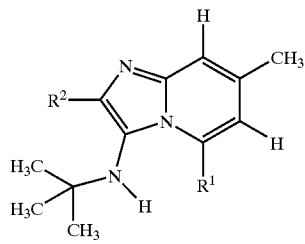

wherein $R^1$ denotes H or a $C_{1-4}$ alkanyl, wherein the alkanyl is straight-chain or branched and is unsubstituted or singly- or multiply-substituted, and $R^2$ denotes a $C_{1-8}$ alkyl, wherein the alkyl is straight-chain or branched, is saturated or unsaturated and is unsubstituted or singly- or multiply-substituted, a $C_{3-8}$ cycloalkyl, wherein the cycloalkyl is saturated or unsaturated and is unsubstituted or singly- or multiply-substituted, a heterocyclyl, wherein the heterocyclyl is saturated or unsaturated and is unsubstituted or singly- or multiply-substituted, an aryl, wherein the aryl is unsubstituted or singly or multiply-substituted, a heteroaryl, wherein the heteroaryl is unsubstituted or singly or multiply-substituted, a $C_{1-8}$ alkyl-$C_{3-8}$ cycloalkyl, a $C_{1-5}$ alkyl-heterocyclyl, a $C_{1-8}$ alkyl-aryl or a $C_{1-6}$ alkyl-heteroaryl, wherein the alkyl is straight-chain or branched, is saturated or unsaturated and is unsubstituted or singly or multiply-substituted, the cycloalkyl is saturated or unsaturated and is unsubstituted or singly or multiply-substituted, the heterocyclyl is saturated or unsaturated and is unsubstituted or singly- or multiply-substituted, the aryl is unsubstituted or singly- or multiply-substituted, and the heteroaryl is unsubstituted or singly- or multiply-substituted, in the form of their bases or of one of their pharmaceutically acceptable salts, constitute very effective NOS inhibitors.

These compounds as such are new, with the exception of the 3-tert.-butyl-amino-substituted imidazo[1,2-a]pyridine of general structure I wherein $R^1$=methyl and $R^2$=phenyl, which has been described by H. Bienyme and K. Bouzid in Angew. Chem 1998), 110, 2349–2352, although without the disclosure of an NOS inhibiting effect (or any other pharmacological or therapeutic effect). Therefore, the present invention also relates to this last-mentioned compound insofar as it relates to the use thereof in a drug, particularly for producing a medication for the inhibition of NO synthase and for the treatment of migraine, septic shock, multiple sclerosis, Parkinson's disease, Alzheimer's disease, Huntington's disease, inflammation, pain due to inflammation, cerebral ischaemia, meningitis, arteriosclerosis and/or for the healing of wounds, and insofar as it relates to a pharmaceutical composition containing said compound.

In the sense of this invention, the expression "$C_{1-8}$ alkyl" comprises acyclic, saturated or unsaturated hydrocarbon radicals which can be branched- or straight-chain and which can be unsubstituted or singly- or multiply-substituted, containing 1 to 8 C atoms, i.e. $C_{1-8}$ alkanyls, $C_{2-8}$ alkenyls and $C_{2-8}$ alkynyls. The alkenyls contain at least one C—C double bond and the alkynyls contain at least one C—C triple bond. The alkyls are advantageously selected from the group comprising methyl, ethyl, n-propyl, 2-propyl, n-butyl, iso-butyl, sec.-butyl, tert.-butyl, n-pentyl, iso-pentyl, neo-pentyl, n-hexyl, 2-hexyl, n-octyl, ethylenyl (vinyl), ethynyl, propenyl (—CH$_2$CH═CH$_2$, —CH═CH—CH$_3$, —C(═CH$_2$)—CH$_3$), propynyl (—CH—C≡CH, —C≡C—CH$_3$), butenyl, butynyl, pentenyl, pentynyl, hexenyl, hexynyl, octenyl and octynyl.

In connection with the present invention, the expression "$C_{1-4}$ alkanyl" comprises saturated, acyclic hydrocarbon radicals containing with 1 to 4 carbon atoms, wherein the radicals are straight-chain or branched and are unsubstituted or singly- or multiply-substituted. The $C_{1-4}$ alkanyl is advantageously methyl, ethyl, n-propyl, 2-propyl, n-butyl, iso-butyl, sec.-butyl or tert.-butyl. $C_{1-4}$ alkanyl most preferably represents methyl.

For the purposes of this invention, the expression "$C_{3-8}$ cycloalkyl" denotes cyclic hydrocarbons containing 3 to 8 carbon atoms, which can be saturated or unsaturated, unsubstituted or singly- or multiply-substituted. $C_{3-8}$ cycloalkyl is advantageously selected from the group comprising cyclopropyl, cyclobutyl, cyclopentyl, cyclohexyl, cycloheptyl, cyclooctyl, cyclopentenyl. cyclohexenyl, cycloheptenyl and cyclooctenyl. Cycloalkyl most preferably represents cyclohexyl.

The expression "heterocyclyl" represents a 3-, 4-, 5-, 6- or 7-membered cyclic organic radical which contains at least 1 hetero atom, or which optionally even contains 2, 3, 4 or 5 hetero atoms, wherein the hetero atoms are identical or different and the cyclic radical is saturated or unsaturated but is not aromatic, and can be unsubstituted or singly- or multiply-substituted. The heterocycle can also be part of a bi- or polycyclic system. The preferred hetero atoms are nitrogen, oxygen and sulphur. The heterocyclyl radical is preferably selected from tetrahydrofuryl, tetrahydropyranyl, pyrrolidinyl, piperidinyl, piperazinyl and morpholinyl, wherein bonding to the compound of general structure I (or III, see below) can occur via any ring member of the heterocyclyl radical.

In the sense of this invention, the expression "aryl" denotes aromatic hydrocarbons, including phenyl, naphthyl and anthracenyl radicals amongst others. These aryl radicals can also be condensed with other saturated, (partially) unsaturated or aromatic ring systems. Each aryl radical can be unsubstituted or can be singly- or multiply-substituted, wherein the aryl substituents can be identical or different and can be situated in any possible position of the aryl. Aryl is advantageously selected from the group comprising phenyl, 1-naphthyl and 2-naphthyl. Aryl radicals which are particularly preferred for the purposes of the invention include phenyl, 3-hydroxyphenyl, 3-methoxyphenyl, 2,3-dihydroxyphenyl, 2,3-dimethoxyphenyl and 1-naphthyl.

The expression "heteroaryl" denotes a 5-, 6- or 7-membered cyclic aromatic radical which contains at least 1 hetero atom and which optionally even contains 2, 3, 4 or 5 hetero atoms, wherein the hetero atoms are identical or different and the heterocycle can be unsubstituted or singly or multiply-substituted. In the case of substitution on the heterocycle, the heteroaryl substituents can be identical or different and can be situated in any possible position of the heteroaryl. The heterocycle can also be part of a bi- or polycyclic system. The preferred hetero atoms are nitrogen, oxygen and sulphur. The heteroaryl-radical is preferably selected from pyrrolyl, furyl, thienyl, pyrazolyl, imidazolyl, pyridinyl, pyridazinyl, pyrimidinyl, pyrazinyl, pyranyl, indotyl, indazolyl, purinyl pyrimidinyl, indolizinyl, quinolinyl, isoquinolinyl, quinazolinyl, carbazolyl, phenazinyl and phenothiazinyl, wherein bonding to compounds of general structure I (or III) can occur via any possible ring member of the heteroaryl radical. Heteroaryl radicals which are particularly preferred for the purposes this invention include pyridin-2-yl, pyridin-3-yl, furan-2-yl, furan-3-yl, 5-hydroxymethylene-furan-2-yl, 5-nitro-furan-2-yl, 5-[1,3]-dioxolan-furan-2-yl, 5-carboxylic acid-furan-2-yl, thien-2-yl (2-thiophen), thien-3-yl (3-thiophen) and 5-carboxylic acid-2-thiophen (5-carboxylic acid-thien-2-yl).

For the purposes of the present invention, the expressions $C_{1-8}$ alkyl-$C_{3-8}$ cycloalkyl", "$C_{1-8}$ alkyl-heterocyclyl", "$C_{1-8}$ alkyl-aryl" and "$C_{1-8}$ alkyl-heteroaryl" signify that $C_{1-8}$ alkyl and cycloalkyl, heterocyclyl, aryl and heteroaryl have the meanings defined above and the cycloalkyl, heterocyclyl, aryl or heteroaryl radical is bonded via a $C_{1-8}$ alkyl group to the compound of general structure I (or III).

In connection with "alkyl", "alkanyl", "alkenyl" and "alkynyl", the term "substituted" in the sense of this invention is to be understood to mean the substitution of a hydrogen radical by F, Cl, Br, I, CN, NH$_2$, or by an NH-alkyl, NH-aryl, NH-heteroaryl, NH-alkyl-aryl, NH-alkyl-heteroaryl, NH-heterocyclyl, NH-alkyl-OH, N(alkyl)$_2$, N-(alkyl-aryl)$_2$, N(alkyl-heteroaryl)$_2$, N(heterocyclyl)$_2$, N(alkyl-OH)$_2$, or by NO, NO$_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(═O)C$_{1-6}$-alkyl, C(═S)C$_{1-6}$-alkyl, C(═O)aryl, C(═S)aryl, C(═O) C$_{1-6}$-alkyl,

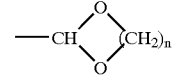

where n=1, 2 or 3, C(═S)C$_{1-6}$-alkyl, C(═S)C$_{1-6}$-alkyl-aryl, C(═O)-heteroaryl, C(═S)-heteroaryl, C(═O)heterocyclyl, C(═S)-heterocyclyl, CO$_2$H, CO$_2$-alkyl, CO$_2$-alkyl-aryl, C(═O)NH$_2$, C(═O)NH-alkyl, C(═O)N-aryl, C(═O)NH-heterocyclyl, C(═O)N(alkyl)$_2$, C(═O)N(alkyl-aryl)$_2$, C(═O)N(alkyl-heteroaryl), C(═O)N(heterocyclyl)$_2$, SO-alkyl, SO$_2$-alkyl. SO$_2$NH$_2$, SO—H, cycloalkyl, aryl, heteroaryl or heterocyclyl, wherein multiply-substituted radicals are to be understood as radicals which are either multiply-, e.g. doubly- or triply-substituted on the same or different atoms, for example triply-substituted on the same C atom as in the case of CF$_3$ or —CH$_2$CF$_3$ or on different sites as in the case of —CH(OH)CH═CH—CHCl$_2$. Multiple substitution can be effected with the same or with different substituents. For the purposes of the present invention, "alkyl" most preferably denotes methyl, ethyl, CH$_2$-OH or CF$_3$ in this connection.

In the sense of this invention, "singly or multiply-substituted"" with respect to "aryl", "heterocyclyl", "heteroaryl" and "alkyl-aryl", and with respect to "cycloalkyl", is to be understood as the single- or multiple substitution, e.g. the double, triple or quadruple substitution of one or more hydrogen atoms of the ring system by F, Cl, Br, I, CN, NH$_2$, NH alkyl, NH-aryl, NH-heteroaryl, NH alkyl-aryl, NH alkyl-heteroaryl, NH-heterocyclyl, NH-alkyl-OH, N(alkyl)$_2$, N-(alkyl-aryl)$_2$, N(alkyl-heteroaryl)$_2$, N(heterocyclyl)$_2$, N(alkyl-OH)$_2$, or by NO, NO$_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(=O)C$_{1-6}$-alkyl, C(=S)C$_{1-6}$-alkyl, C(=O)aryl, C(=S)aryl, C(=O)C$_{1-6}$-alkyl,

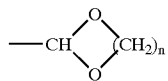

where n=1, 2 or 3, C(=S)C$_{1-6}$-alkyl, C(=S)C$_{1-6}$-alkyl-aryl, C(=O)-heteroaryl, C(=S)-heteroaryl, C(=O)heterocyclyl, C(=S)-heterocyclyl, CO$_2$H, CO$_2$-alkyl, CO$_2$-alkyl-aryl, C(=O)NH$_2$, C(=O)NH-alkyl, C(=O)N-aryl, C(=O)NH-heterocyclyl, C(=O)N(alkyl)$_2$, C(=O)N(alkyl-aryl)$_2$, C(=O)N(alkyl-heteroaryl), C(=O)N(heterocyclyl)$_2$, SO-alkyl, SO$_2$-alkyl. SO$_2$NH$_2$, SO—H, cycloalkyl, aryl, heteroaryl or heterocyclyl; on one atom or optionally on different atoms (wherein a substituent can optionally be substituted itself). Multiple substitution is effected with the same or with different substituents. The substituents which are particularly preferred for "aryl" are F, —CF$_3$, —OH and —O—CH$_3$. The substituents which are particularly preferred for "heteroaryl" are OH, —O—CH$_3$, —CH$_2$OH, —NO$_2$, —CO$_2$H, —CO$_2$ethyl and -[1,3]-dioxolan. The substituents which are particularly preferred for "cycloalkyl" are CO$_2$H and CO$_2$ethyl.

Pharmaceutically acceptable salts in the sense of this invention are those salts of the compounds according to the invention of general structure I which are pharmaceutically acceptable or physiologically compatible when administered to mammals, including humans. Pharmaceutically acceptable salts such as these can be formed with inorganic or organic acids for example.

Pharmaceutically acceptable salts of the compounds according to the invention of general structure I are preferably formed with hydrochloric acid, hydrobromic acid, sulphuric acid, phosphoric acid, methanesulphonic acid, p-toluenesulphonic acid, carbonic acid, formic acid, acetic acid, oxalic acid. succinic acid, tartaric acid, mandelic acid, fumaric acid, lactic acid, citric acid, glutamic acid or aspartic acid. The salts which are formed, amongst others, include hydrochlorides, hydrobromides, phosphates, carbonates, hydrogen carbonates, formates, acetates, oxalates, succinates, tartrates, fumarates, citrates and glutamates. Solvates are also preferred, particularly hydrates of the compounds according to the invention which can be obtained by crystallisation from aqueous solution, for example.

If the compounds according to the invention of general structure I comprise at least one centre of asymmetry, they can be present in the form of their racemates, in the form of the pure enantiomers and/or diastereomers or in the form of mixtures of said enantiomers or diastereomers, both as such and as pharmaceutically acceptable salts of these compounds. The mixtures can comprise any mixture ratio of stereoisomers. Chiral compounds of general structure I are preferred as pure enantiomeric compounds.

The compounds which are preferred according to the present invention are those 3-tert.-butyl-amino-substituted imidazo[1,2-a]pyridines of general structure I in which R$^1$ denotes H or methyl, either in the form of their bases or in the form of acceptable pharmaceutical salts.

The compounds which are particularly preferred from these preferred compounds are those in which R$^2$ represents an for aryl or heteroaryl, particularly phenyl, 1-naphthyl, furyl, thienyl or pyridinyl. These radicals are most preferably unsubstituted or are singly- or doubly-substituted with —F, —CF$_3$, —OH, —OCH$_3$, —CH$_2$OH, —NO$_2$, —CO$_2$H or -[1,3]-dioxoan, wherein double substitution can be effected with the same or with different substituents. These compounds according to the invention can also exist in the form of their bases or pharmaceutically acceptable salts.

The compounds according to the present invention which are most particularly preferred are substances of general structure I in the form of their bases or pharmaceutically acceptable salts, which are selected from the following group:

tert.-butyl-(7-methyl-2-pyridin-3-yl-imidazo[1,2-a]pyridin-3-yl)-amine, tert.-butyl-[2-(2,3-dimethoxy-phenyl)-5,7-dimethyl-imidazo[1,2-a]pyridin-3-yl]-amine, 3-(3-tert.-butylamino-5,7-dimethyl-imidazo[1,2-a]pyridin-2-yl)-phenol, 3-(3-tert.-butylamino-7-methyl-imidazo[1,2-a]pyridin-2-yl)-phenol, tert.-butyl-(2-furan-2-yl-5,7-dimethyl-imidazo[1,2-a]pyridin-3-yl)-amine, tert.-butyl-(7-methyl-2-naphthalen-1-yl-imidazo[1,2-a]pyridin-3-yl) amine, tert.-butyl-(5,7-dimethyl-2-(5-nitro-furan-2-yl)-imidazo[1,2-a]pyridin-3-yl] -amine,

[5-(3-tert.-butylamino-7-methyl-imidazo[1,2-a]pyridin-2-yl)-furan-2-yl]-methanol, tert.-butyl-[2-(5-[1,3]dioxolan-2-yl-furan-2-yl)-7-methyl-imidazo[1,2-a]-pyridin-3-yl]-amine,

[5-(3-tert.-butylamino-5,7-dimethyl-imidazo[1,2-a]pyridin-2-yl)-furan-2-carboxylic acid, tert.-butyl-(2-furan-2-yl-7-methyl-imidazo[1,2-a]pyridin-3-yl)-amine, tert.-butyl-(7-methyl-2-pyridin-2-yl-imidazo[1,2-a]pyridin-3-yl)-amine, 5-(3-tert.-butylamino-7-methyl-imidazo[1,2-a]pyridin-2-yl)-thiophen-2-carboxylic acid, and tert.-butyl-(7-methyl-2-phenyl-imidazo[1,2-a]pyridin-3-yl)-amine.

Other preferred compounds of general structure I in the form of their bases or of their pharmaceutically acceptable salts are selected from the following group:

tert-butyl-(2,5,7-tri-methyl-imidazo[1,2-a]pyridin-3-yl)-amine, tert.-butyl-(2-cyclohexyl-5,7-dimethyl-imidazo[1,2-a]pyridin-3-yl)-amine, tert.-butyl-(2-cyclohexyl-7-methyl-imidazo[1,2-a]pyridin-3-yl)-amine, tert.-butyl-(2,7-dimethyl-imidazo[1,2-a]pyridin-3-yl)-amine, The present invention also relates to a method of producing a compound of general structure I

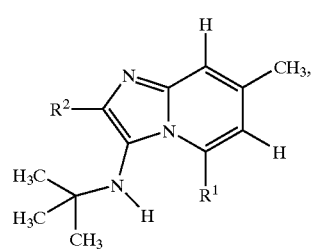

I wherein said method is characterised in that an aminopyridine of general structure II

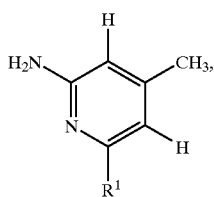

wherein

R¹ denotes H or a $C_{1-4}$ alkanyl, wherein the alkanyl is straight-chain or branched and is unsubstituted or singly- or multiply-substituted, is reacted with an aldehyde of general structure III

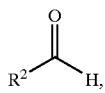

wherein

R² denotes a $C_{1-8}$ alkyl, wherein the alkyl is straight-chain or branched, is saturated or unsaturated and is unsubstituted or singly- or multiply-substituted; a $C_{3-8}$ cycloalkyl, wherein the cycloalkyl is saturated or unsaturated and is unsubstituted or singly- or multiply-substituted; a heterocyclyl, wherein the heterocyclyl is saturated or unsaturated and is unsubstituted or singly- or multiply-substituted; an aryl, wherein the aryl is unsubstituted or singly or multiply-substituted; a heteroaryl, wherein the heteroaryl is unsubstituted or singly or multiply-substituted; a $C_{1-8}$ alkyl-$C_{3-8}$ cycloalkyl; a $C_{1-5}$ alkyl-heterocyclyl; a $C_{1-8}$ alkyl-aryl or a $C_{1-6}$ alkyl-heteroaryl, wherein the alkyl is straight-chain or branched, is saturated or unsaturated and is unsubstituted or singly or multiply-substituted, the cycloalkyl is saturated or unsaturated and is unsubstituted or singly or multiply-substituted, the heterocyclyl is saturated or unsaturated and is unsubstituted or singly- or multiply-substituted, the aryl is unsubstituted or singly- or multiply-substituted, and the heteroaryl is unsubstituted or singly- or multiply-substituted, with the proviso that R² does not denote phenyl if R¹ denotes methyl, and with tert.-butyl isonitrile of structure IV

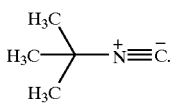

The method according to the invention is preferably carried out in the presence of an inorganic or organic Lewis or protonic acid, particularly in the presence of perchloric acid, which is preferably used as a 20% aqueous solution.

The three-component reaction according to the invention is preferably conducted as a "one-pot" process, wherein an aminopyridine of general structure II with is reacted with an aldehyde of general structure III and isonitrile of general structure IV simultaneously.

The method according to the invention can also be conducted in a semi- or fully-automated manner as a parallel synthesis of a group of compounds of general structure I according to the invention.

The method according to the invention can be conducted in the absence of solvents. The method is preferably conducted in an organic solvent, however, particularly in dichloromethane or acetonitrile. The reaction temperature and reaction time are preferably selected so that the starting materials react as completely as possible. The reaction temperature preferably ranges from 0° C. to 80° C., particularly from 10° C. to 35° C. The reaction time usually ranges between 5 minutes and 24 hours.

The aminopyridines of general structure II, the aldehydes of general structure III and the tert.-butyl isonitrile of structure IV which are used in the method according to the invention are commercially available (from e.g. Acros, Geel; Avocado, Port of Heysham; Aldrich, Deisenhofen; Fluka, Seelze; Lancaster; Mulheim; Maybridge, Tintagel; Merck, Darmstadt; Sigma, Deisenhofen; or TCI, Japan) or can be produced by methods which are generally known in the prior art.

The compounds of general structure I according to the invention can be isolated either as a free base or as a salt. The free base of a compound of general structure I according to the invention is usually obtained after completion of the reaction by the method according to the invention as described above, by subsequent conventional work-up. The free base which is thus obtained or which is formed in-situ without isolation can then be converted into the corresponding salt by reaction with an inorganic or organic acid, preferably with hydrochloric acid, hydrobromic acid, sulphuric acid, phosphoric acid, methanesulphonic acid, p-toluenesulphonic acid, carbonic acid, formic acid, acetic acid, oxalic acid, succinic acid, tartaric acid, mandelic acid, fumaric acid, lactic acid, citric acid, glutamic acid or aspartic acid, for example. The salts which are formed include hydrochlorides, hydrobromides, phosphates, carbonates, hydrogen carbonates, formates, acetates, oxalates, succinates, tartrates, fumarates, citrate and glutamates. Hydrochloride formation, which is particularly preferred, can also be effected by treating the base, dissolved in organic solvent such as butan-2-one (methyl ethyl ketone), with trimethylsilyl chloride (TMSCl).

If the compounds of general structure I are obtained in the production method according to the invention as racemates or as mixtures of different enantiomers and/or diastereomers, these mixtures can be separated by method which are well known in the prior art. Examples of suitable methods include chromatographic methods of separation, particularly liquid chromatography methods under normal or elevated pressure, preferably MPLC and HPLC methods, or by methods of fractional crystallisation. In particular, individual enantiomers can be separated from each other, for example, by means of HPLC on a chiral phase or by the crystallisation of diastereoisomeric salts which are formed with chiral acids, for instance (+)-tartaric acid, (−)-tartaric acid or (+)-camphorsulphonic acid.

The present invention also relates to a drug which contains at least one compound of general structure I in the form of its base or of a pharmaceutically acceptable salt

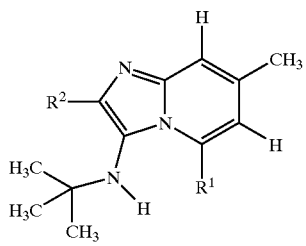

wherein
R¹ denotes H or a $C_{14}$ alkanyl, wherein the alkanyl is straight-chain or branched and is unsubstituted or singly- or multiply-substituted, and R² denotes a $C_{1-8}$ alkyl, wherein the alkyl is straight-chain or branched, is saturated or unsaturated and is unsubstituted or singly- or multiply-substituted, a $C_{3-8}$ cycloalkyl, wherein the cycloalkyl is saturated or unsaturated and is unsubstituted or singly- or multiply-substituted, a heterocyclyl, wherein the heterocyclyl is saturated or unsaturated and is unsubstituted or singly- or multiply-substituted, an aryl, wherein the aryl is unsubstituted or singly or multiply-substituted, a heteroaryl, wherein the heteroaryl is unsubstituted or singly or multiply-substituted, a $C_{1-8}$ alkyl-$C_{3-8}$ cycloalkyl, a $C_{1-5}$ alkyl-heterocyclyl, a $C_{1-8}$ alkyl-aryl or a $C_{1-6}$ alkyl-heteroaryl, wherein the alkyl is straight-chain or branched, is saturated or unsaturated and is unsubstituted or singly or multiply-substituted, the cycloalkyl is saturated or unsaturated and is unsubstituted or singly or multiply-substituted, the heterocyclyl is saturated or unsaturated and is unsubstituted or singly- or multiply-substituted, the aryl is unsubstituted or singly- or multiply-substituted, and the heteroaryl is unsubstituted or singly- or multiply-substituted. The drug preferably contains the compound of general structure I according to the invention in the form of its hydrochloride salt.

The drug according to the invention most preferably contains a compound in the form of its base or of a pharmaceutically acceptable salt, particularly in the form of its hydrochloride, which is selected from tert.-butyl-(7-methyl-2-pyridin-3-yl-imidazo[1,2-a]pyridin-3-yl)-amine, tert.-butyl-[2-(2, 3-dimethoxy-phenyl)-5,7-dimethyl-imidazo[1,2-a]pyridin-3-yl] -amine, tert-butyl-(2,5,7-trimethyl-imidazo[1,2-a]pyridin-3-yl)-amine, 3-(3-tert.-butylamino-5,7-dimethyl-imidazo[1,2-a]pyridin-2-yl)-phenol, tert.-butyl-(2-cyclohexyl-5,7-dimethyl-imidazo[1,2-a]pyridin-3-yl)-amine, 3-(3-tert.-butylamino-7-methyl-imidazo[1,2-a]pyridin-2-yl)-phenol, tert.-butyl-(2-furan-2-yl-5,7-dimethyl-imidazo[1,2-a]pyridin-3-yl)-amine, tert.-butyl-(7-methyl-2-naphthalen-1-yl-imidazo[1,2-a]pyridin-3-yl) amine, tert.-butyl-(5,7-dimethyl-2-(5-nitro-furan-2-yl)-imidazo[1,2-a]pyridin-3-yl]-amine,

[5-(3-tert.-butylamino-7-methyl-imidazo[1,2-a]pyridin-2-yl)-furan-2-yl]-methanol, tert.-butyl-[2-(5-[1,3] dioxolan-2-yl-furan-2-yl)-7-methyl-imidazo[1,2-a]-pyridin-3-yl]-amine,

[5-(3-tert.-butylamino-5,7-dimethyl-imidazo[1,2-a]pyridin-2-yl)-furan-2-carboxylic acid, tert.-butyl-(2-furan-2-yl-7-methyl-imidazo[1,2-a]pyridin-3-yl)-amine, tert.-butyl-(7-methyl-2-pyridin-2-yl-imidazo[1,2-a]pyridin-3-yl)-amine, tert.-butyl-(2-cyclohexyl-7-methyl-imidazo[1,2-a]pyridin-3-yl)-amine, tert.-butyl-(2, 7-dimethyl-imidazo[1,2-a]pyridin-3-yl)-amine, 5-(3-tert.-butylamino-7-methyl-imidazo[1,2-a]pyridin-2-yl)-thiophen-2-carboxylic acid, tert.-butyl-(7-methyl-2-phenyl-imidazo[1,2-a]pyridin-3-yl)-amine.

The present invention further relates to method of using a compound of general structure I

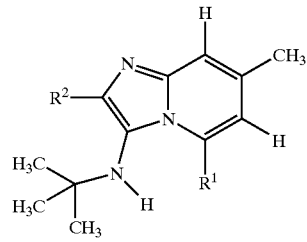

wherein
R¹ denotes H or a $C_{14}$ alkanyl, wherein the alkanyl is straight-chain or branched and is unsubstituted or singly- or multiply-substituted, and R² denotes a $C_{1-8}$ alkyl, wherein the alkyl is straight-chain or branched, is saturated or unsaturated and is unsubstituted or singly- or multiply-substituted, a $C_{3-8}$ cycloalkyl, wherein the cycloalkyl is saturated or unsaturated and is unsubstituted or singly- or multiply-substituted, a heterocyclyl, wherein the heterocyclyl is saturated or unsaturated and is unsubstituted or singly- or multiply-substituted, an aryl, wherein the aryl is unsubstituted or singly or multiply-substituted, a heteroaryl, wherein the heteroaryl is unsubstituted or singly or multiply-substituted, a $C_{1-8}$ alkyl-$C_{3-8}$ cycloalkyl, a $C_{1-5}$ alkyl-heterocyclyl, a $C_{1-8}$ alkyl-aryl or a $C_{1-6}$ alkyl-heteroaryl, wherein the alkyl is straight-chain or branched, is saturated or unsaturated and is unsubstituted or singly or multiply-substituted, the cycloalkyl is saturated or unsaturated and is unsubstituted or singly or multiply-substituted, the heterocyclyl is saturated or unsaturated and is unsubstituted or singly- or multiply-substituted, the aryl is unsubstituted or singly- or multiply-substituted, and the heteroaryl is unsubstituted or singly- or multiply-substituted, or a pharmaceutically acceptable salt thereof, including possible stereoisomers or racemic or non-racemic mixtures of stereoisomers, for inhibiting NO synthase.

The compound of general structure I according to the invention have surprisingly proved to be effective NOS inhibitors.

A compound of general structure I which is particularly preferred for the inhibition method according to the invention is:

tert.-butyl-(7-methyl-2-pyridin-3-yl-imidazo[1,2-a]pyridin-3-yl)-amine, tert.-butyl-[2-(2,3-dimethoxy-phenyl)-5,7-dimethyl-imidazo[1,2-a]pyridin-3-yl]-amine, tert-butyl-(2,5,7-trimethyl-imidazo[1,2-a]pyridin-3-yl)-amine, 3-(3-tert.-butylamino-5,7-dimethyl-imidazo[1,2-a]pyridin-2-yl)-phenol, tert.-butyl-(2-cyclohexyl-5,7-dimethyl-imidazo[1,2-a]pyridin-3-yl)-amine, 3-(3-tert.-butylamino-7-methyl-imidazo[1,2-a]pyridin-2-yl)-phenol, tert.-butyl-(2-furan-2-yl-5,7-dimethyl-imidazo[1,2-a]pyridin-3-yl)-amine, tert.-butyl-(7-methyl-2-naphthalen-1-yl-imidazo[1,2-a]pyridin-3-yl) amine, tert.-butyl-(5,7-dimethyl-2-(5-nitro-furan-2-yl)-imidazo[1,2-a]pyridin-3-yl]-amine,

[5-(3-tert.-butylamino-7-methyl-imidazo[1,2-a]pyridin-2-yl)-furan-2-yl]-methanol, tert.-butyl-[2-(5-[1,3]dioxolan-2-yl-furan-2-yl)-7-methyl-imidazo[1,2-a]-pyridin-3-yl]-amine,

[5-(3-tert.-butylamino-5,7-dimethyl-imidazo[1,2-a]pyridin-2-yl)-furan-2-carboxylic acid, tert.-butyl-(2-furan-2-yl-7-methyl-imidazo[1,2-a]pyridin-3-yl)-amine, tert.-butyl-(7-methyl-2-pyridin-2-yl-imidazo[1,2-a]pyridin-3-yl)-amine, tert.-butyl-(2-cyclohexyl-7-methyl-imidazo[1,2-a]pyridin-3-yl)-amine, tert.-butyl-(2, 7-dimethyl-imidazo[1,2-a]pyridin-3-yl)-amine, 5-(3-tert.-butylamino-7-methyl-imidazo[1,2-a]pyridin-2-yl)-thiophen-2-carboxylic acid, or tert.-butyl-(7-methyl-2-phenyl-imidazo[1,2-a]pyridin-3-yl)-amine, or a pharmaceutically acceptable salt thereof.

In particular, the 3-tert.-butyl-amino-substituted imidazo[1,2-a]pyridines of general structure I according to the invention 1 can be used in the form its free base or of one of its pharmaceutically acceptable salts for producing a medication and for the treatment of migraine. For this purpose, the compounds are most preferably selected from the group comprising:

tert.-butyl-(7-methyl-2-pyridin-3-yl-imidazo[1,2-a]pyridin-3-yl)-amine, tert.-butyl-[2-(2,3-dimethoxy-phenyl)-5,7-dimethyl-imidazo[1,2-a]pyridin-3-yl]-amine, tert-butyl-(2,5,7-trimethyl-imidazo[1,2-a]pyridin-3-yl)-amine, 3-(3-tert.-butylamino-5,7-dimethyl-imidazo[1,2-a]pyridin-2-yl)-phenol, tert.-butyl-(2-cyclohexyl-5,7-dimethyl-imidazo[1,2-a]pyridin-3-yl)-amine, 3-(3-tert.-butylamino-7-methyl-imidazo[1,2-a]pyridin-2-yl)-phenol, tert.-butyl-(2-furan-2-yl-5,7-dimethyl-imidazo[1,2-a]pyridin-3-yl)-amine, tert.-butyl-(7-methyl-2-naphthalen-1-yl-imidazo[1,2-a]pyridin-3-yl) amine, tert.-butyl-(5,7-dimethyl-2-(5-nitro-furan-2-yl)-imidazo[1,2-a]pyridin-3-yl]-amine,

[5-(3-tert.-butylamino-7-methyl-imidazo[1,2-a]pyridin-2-yl)-furan-2-yl]-methanol, tert.-butyl-[2-(5-[1,3] dioxolan-2-yl-furan-2-yl)-7-methyl-imidazo[1,2-a]-pyridin-3-yl]-amine,

[5-(3-tert.-butylamino-5,7-dimethyl-imidazo[1,2-a]pyridin-2-yl)-furan-2-carboxylic acid, tert.-butyl-(2-furan-2-yl-7-methyl-imidazo[1,2-a]pyridin-3-yl)-amine, tert.-butyl-(7-methyl-2-pyridin-2-yl-imidazo[1,2-a]pyridin-3-yl)-amine, tert.-butyl-(2-cyclohexyl-7-methyl-imidazo[1,2-a]pyridin-3-yl)-amine, tert.-butyl-(2,7-dimethyl-imidazo[1,2-a]pyridin-3-yl)-amine, 5-(3-tert.-butylamino-7-methyl-imidazo[1,2-a]pyridin-2-yl)-thiophen-2-carboxylic acid, tert.-butyl-(7-methyl-2-phenyl-imidazo[1,2-a]pyridin-3-yl)-amine.

Moreover, the compounds of general structure I according to the invention are also suitable for producing medications for the treatment of septic shock, multiple sclerosis, Parkinson's disease, Alzheimer's disease, Huntington's disease, inflammation, pain due to inflammation, cerebral ischaemia, diabetes, meningitis, arteriosclerosis and/or for the healing of wounds.

The present invention also relates to pharmaceutical compositions which contain at least one compound of general structure I as defined above in the form of its base or of one of its pharmaceutically acceptable salts and which contain one or more pharmaceutical adjuvants or excipients.

The drugs and pharmaceutical compositions according to the invention can be present and can be administered as liquid, semi-solid or solid drug forms, and in the form of injection solutions, drops, juices, syrups, sprays, suspensions, granules, tablets, pellets, patches, capsules, plasters, suppositories, ointments, creams, lotions, gels, emulsions or aerosols. Depending on their drug form, in addition to at least one compound of general structure according to the invention, the pharmaceutical compositions may contain pharmaceutical adjuvants such as carrier materials, fillers, solvents, diluents, surface-active substances, colorants, preservatives, disintegrating agents, internal lubricants, lubricants, flavourings and/or binders. These adjuvants may, for example, comprise water, ethanol. 2-propanol, glycerol, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, pharmaceutically acceptable natural and synthetic rubbers, gum Arabic, alginates, dextran, saturated and unsaturated fatty acids, stearic acid, magnesium stearate, zinc stearate, glyceryl stearate, sodium lauryl sulphate, edible oils, sesame oil, coconut oil, peanut oil, soya oil, lecithin, sodium lactate, polyoxyethylene- and poly-propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silica, titanium dioxide, magnesium sulphate, zinc sulphate, calcium sulphate, potash, calcium phosphate, dicalcium phosphate, potassium bromide, potassium iodide, french chalk, kaolin, pectin, crospovidon, agar and bentonite.

The choice of adjuvants, as well as the amount thereof to be used, depends on whether the drug is to be administered orally, subcutaneously, parenterally, intravenously, intraperitoneally, intradermally, intramuscularly, intranasally, buccally, rectally or locally, for example for infections of the skin, mucous membranes and eyes. Preparations in the form of tablets, dragees, capsules, granules, drops, juices, syrups, etc. are suitable for oral administration. Solutions, suspensions, easily reconstitutable dry preparations and sprays are suitable for parenteral and topical application and for application by inhalation. Compounds of general structure I according to the invention in a deposit in dissolved form or in a patch, optionally with the addition of agents which promote dermal penetration, are suitable preparations for percutaneous application. Forms of preparation which can be used orally or percutaneously are capable of effecting delayed release of the compounds of general structure I according to the invention.

The drugs and pharmaceutical compositions according to the invention are produced with the aid of media which are well known in the art of pharmaceutical formulation. Suitable apparatuses, methods and procedures include those described, for example in "Remington's Pharmaceutical Sciences", edited by A. R. Gennaro, 17th Edition, Mack Publishing Company, Easton. Pa. (1985), particularly those described in Part 8, Chapters 76 to 93, which are incorporated herein by reference.

Thus for a solid formulation such as a tablet, for example, the active ingredient of the drug, i.e. a compound of general structure I or of one of its pharmaceutically acceptable salts, can be mixed with a pharmaceutical carrier, e.g. with conventional tablet constituents such as maize starch, lactose, saccharose, sorbitol, French chalk, magnesium stearate, dicalcium phosphate or gum, and with pharmaceutical diluents such as water, in order to form a solid preformulation composition which contains a compound according to the invention or a pharmaceutically acceptable salt thereof in a homogeneous distribution. The term "homogeneous distribution" is to be understood here to mean that the active ingredient is distributed uniformly over the entire preformulation composition, so that the latter can be subdivided directly into unit dose forms of the same strength, such as tablets, pills or capsules. The solid preformulation composition is subsequently subdivided into unit dose forms. The tablets or pills of the drug according to the invention or of the compositions according to the invention can also be coated or compounded in other ways in order to prepare a form of dosage which exhibits delayed release. Examples of suitable coating media include polymeric acids and mixtures of polymeric acids with materials such as shellac, cetyl alcohol and/or cellulose acetate.

The amount of active ingredient to be administered to the patient varies, and depends on the weight, age and medical history of the patient, as well as on the type of administration, the indication and the severity of the illness. 0.1 to 5000 mg/kg, particularly 1 to 500 mg/kg, preferably 2 to 250 mg/kg body weight of at least one compound of general structure I according to the invention is usually administered.

The assays used for determining NOS inhibition by compounds of general structure I according to the invention are described below:

NOS Assay

General

This assay enabled the percentage inhibition of NO synthase to be determined by measuring the NOS activity on the action of the active ingredient. NO synthase was mixed with radioactively labelled arginine and the active ingredient under suitable conditions. After terminating the NO-forming reaction at a predetermined time, the amount of unreacted arginine was determined directly or indirectly. Comparison of this amount with the amount of arginine remaining from a mixture of NOS and arginine without the addition of active ingredient but under conditions which were otherwise the same gave the % inhibition of NO synthase by the active ingredient tested. This assay was performed as follows:

(a) Incubation of NO synthase, with labelled arginine as a substrate, in a reaction vessel.
(b) Separation of the labelled arginine from any labelled citrulline which was formed as a product of the enzymatic reaction at a time at which the concentration of citrulline was increasing.
(c) Measuring the amount of arginine separated in each case.

Separation was effected through a filter plate membrane.

This NOS assay was particularly suitable for "High Throughput Screening" (HTS) on microtitration plates (MTPs).

HTS-NOS Assay: General Procedure

In this HTS-NOS assay, radioactive arginine was used as the substrate. The assay volume can be selected within the range from 25 pl and 250 pl depending on the type of microtitration plate (MTP). Cofactors and coenzymes were added depending on the enzyme source used. Batches were incubated in this microtitration plate (assay MTP) according to step (a) at room temperature, for between 5 and 60 minutes depending on the enzyme activity (units) employed. At the end of the incubation (step (a)) the plate was placed in a cell harvester which was fitted with an MTP comprising a cation exchange membrane filter base (filter MTP). All the batches from the assay MTP were transferred to this filter MTP and were filtered off under suction through a cation exchange filter plate comprising a paper filter containing phosphate groups. The filter MTP was subsequently washed with a buffer or with water. By means of this procedure, the remaining arginine substrate was bound to the cation exchanger, whilst the enzymatically formed radioactive citrulline was quantitatively removed by washing. After drying the filter MTP and adding a scintillation liquid, the bound arginine was counted in a scintillation counter. An uninhibited NOS reaction was manifested by a low level of radioactivity. An inhibited enzyme reaction meant that the radioactive arginine had not reacted, i.e. the filter contained a high level of radioactivity.

| Materials used |
|---|
| arginine: L-[2,3,4-$^3$H] monohydrochloride, Cat. No. NET-1123, supplied by NEN |
| anhydrous $CaCl_2$: Cat.- No. 2388.1000: supplied by Merck KGaA |
| 1,4-dithiothreitol (DTT): Cat. No. 708984, supplied by ROCHE |
| $Na_2$EDTA dihydrate: Cat. No. 03680: supplied by FLUKA |
| HEPES: Cat. No. H-3375; supplied by SIGMA |
| NADPH, tetrasodium salt: Cat. No. 1585363; supplied by ROCHE |
| TRIS: Cat. No. 93349; supplied by FLUKA |

| | |
|---|---|
| Enzyme preparation buffer: | 50 mM Tris-HCl with 1 mM EDTA: the pH of the buffer was set to 7.4 at 4° C. |
| Incubation buffer (medium): | 50 mM HEPES with 1 mM EDTA; 1.25 mM $CaCl_2$ and 1 mM dithiothreitol. The pH of the buffer was set to 7.4 at 25° C. |
| Washing medium: | $H_2O$ |

Enzyme Preparation

Rat cerebellum was used as the starting tissue. The animals were stunned and killed, and the brain tissue, namely the cerebellum, was removed. 1 ml enzyme preparation buffer was added to each rat cerebellum, and the batch was digested in a Polytron homogeniser for 1 minute at 6000 rpm. This was followed by centrifugation at 4° C. for 15 minutes at 20,000 g. The supernatant was subsequently removed by decantation and portions thereof were frozen at −80° C. (the precipitate was discarded).

Incubation Batch 96-well MTPs were used, which had a well capacity of ≦250 µl Sequence of additions by pipette: see Table 1:

TABLE 1

| Substance | Molarity of batch | µl | *Protein in batch |
|---|---|---|---|
| incubation buffer | — | 100 | — |
| test substance | variable; preferably $10^{-5}$M 0.5 embodiment | variable; preferably 20 µl | — |
| NADPH | | 20 | — |
| enzyme (see Example 3) | — | variable: max. volume of enzyme solution = 50 µl | variable; maximum usable amount of protein = 100 µg |
| [$^3$H] substrate | variable; preferably 50 nM | variable; preferably 10 µl | — |
| Final volume | | 250 µl max. | |

*Protein quantification was conducted according to methods, described in O.H. Lowry et al: J. Biol. Chem. 193, 265 (1951)

After the addition by pipette was complete, a cover was placed on the MTP (assay MTP). Incubation was conducted at 25° C. (room temperature (RT)) for 5–60 minutes depending on the amount and activity of the enzyme used.

The contents of the assay MTP were subsequently transferred by means of a 96-well cell harvester into a 96-well cation exchanger MTP (filter MTP) and was filitered under suction. This was followed by washing once with 200 ml $H_2O$ (from a basin). The plate was then dried for 1 hour at 60° C. in a drying oven. The base of the filter MTP was then sealed exactly from below with a "back seal". Thereafter, 35 pl of scintillator were added by pipette to each well. The top surface of the plate was also sealed with a top seal. After a holding time of 1 hour, the plate was measured in a βcounter.

In HTS operation, the incubation medium, NADPH and enzyme solution were combined before the commencement of the pipetting step so as not to have to perform three separate, time-consuming pipetting operations.

The results obtained in the NOS assay on examples of compounds are given in Table 2.

Citrulline Assay

This assay was performed as described by D. S. Bredt and S. H. Snyder (*Proc. Natl. Acad. Sci. USA* (1990), 87, 682–85). The results of the citrulline assay for examples of compounds are listed in Table 2.

The following examples serve to explain the invention in greater detail, without limiting the invention.

EXAMPLES

Compounds according to the invention were prepared by the following general synthesis procedures (GSPs).

General Experimental Procedure 1 (GSP 1)

A small, round-bottomed glass tube (diameter 16 mm, length 125 mm) with a screw thread was fitted with a stirrer and was sealed by a screw cap comprising a septum. The tube was placed in a reactor block maintained at 15° C. The following reagents were added in succession by pipette:

1.) 1 ml of an 0.1 M solution of aminopyridine II+20% $HClO_4$ in dichloromethane,
2.) 0.5 ml of an 0.3 M solution of aldehyde III in dichloromethane, and
3.) 0.575 ml of an 0.2 M solution of tert.-butyl isonitrile in dichloromethane.

The reaction mixtures were stirred for 12 hours at 15° C. Thereafter, the reaction solution was filtered off. During filtration, the tubes were washed twice with 1 ml dichloromethane and 200 µl water each time.

The reaction mixture was treated with 3 ml of a 10% NaCl solution and 1.5 ml dichloromethane, and thoroughly mixed. The organic phase was removed and the aqueous phase was again extracted with 1.5 ml dichloromethane. The combined organic phases were dried over 2.4 g (granular) $MgSO_4$. The solvent was removed in a vacuum centrifuge.

The chemicals and solvents used were acquired commercially. Each substance was analysed by ESI MS and/or NMR.

Examples 1–17, which were prepared by GSP 1, were tested automatically by HTS-NOS assay. The results are given in Table 2.

TABLE 2

| Example No. | Compound | HTS-NOS assay: %-inhibition (10 µm) | Mass calculated | Masse found |
|---|---|---|---|---|
| 1 | tert-butyl-(7-methyl-2-pyridin-3-yl-imidazo[1,2-a]pyridin-3-yl)-amine | 63 | 280.37 | 281.3 |
| 2 | tert-butyl-(2-(2,3-dimethoxy-phenyl)-5,7-dimethyl-imidazo[1,2-a]pyridin-3-yl]-amine | 61 | 353.46 | 354.2 |
| 3 | tert-butyl-(2,5,7-trimethyl-imidazo[1,2-a]pyridin-3-yl)-amine | 67 | 231.34 | 232.2 |
| 4 | 3-(3-tert-butylamino-5,7-dimethyl-imidazo[1,2-a]pyridin-2-yl)-phenol | 64 | 309.41 | 310.3 |
| 5 | tert-butyl-(2-cyclohexyl-5,7-dimethyl-imidazo[1,2-a]pyridin-3-yl)-amine | 63 | 299.46 | 300.3 |
| 6 | 3-(3-tert-butylamino-7-methyl-imidazo[1,2-a]pyridin-2-yl)-phenol | 59 | 295.38 | 296.3 |
| 7 | tert-butyl-(2-furan-2-yl-5,7-dimethyl-imidazo[1,2-a]pyridin-3-yl)-amine | 60 | 283.37 | 284.2 |
| 8 | tert-butyl-(7-methyl-2-naphthalen-1-yl-imidazo[1,2-a]pyridin-3-yl)-amine | 67 | 329.44 | 330.4 |

TABLE 2-continued

| Example No. | Compound | HTS-NOS assay: %-inhibition (10 μm) | Mass calculated | Masse found |
|---|---|---|---|---|
| 9 | tert-butyl-[5,7-dimethyl-2-(5-nitro-furan-2-yl)-imidazo[1,2-a]pyridin-3-yl-amine | 59 | 328.37 | 329.4 |
| 10 | [5-(3-tert-butyl-7-methyl-imidazo[1,2-a]pyridin-2-yl)-furan-2-yl]-methanol | 52 | 299.37 | 300.3 |
| 11 | tert-butyl-[2-(5-[1,3]dioxolan-2-yl-furan-2-yl)-7-methyl-imidazo[1,2-a] pyridin-3-yl]-amine | 62 | 341.41 | 342.4 |
| 12 | 5-(3-tert-butylamino-5,7-dimethyl-imidazo[1,2-a]pyridin-2-yl)-furan-2-carboxylic acid | 56 | 327.38 | 328.3 |
| 13 | tert-butyl-(2-furan-2-yl-7-methyl-imidazo[1,2-a]pyridin-3-yl)-amine | 57 | 269.34 | 270.4 |
| 14 | tert-butyl-(7-methyl-2-pyridin-2-yl-imidazo[1,2-a]pyridin-3-yl)-amine | 67 | 280.37 | 281.3 |
| 15 | tert-butyl-(2-cyclohexyl-7-methyl-imidazo[1,2-a]pyridin-3-yl)-amine | 52 | 285.43 | 286.4 |
| 16 | tert-butyl-(2,7-dimethyl-imidazo[1,2-a]pyridin-3-yl)-amine | 65 | 217.31 | 218.2 |
| 17 | 5-(3-tert-butylamino-7-methyl-imidazo[1,2-a]pyridin-2-yl)-thiophen-12-carboxylic acid | 61 | 329.42 | 330.3 |

As a comparison example, 7-nitroindazole was tested by NOS assay, and exhibited an inhibition (10 μM) of 50%

General Experimental Procedure 2 (GSP 2)

(Equivalents denote quantities of substance equivalent to the tert-butyl isonitrile IV used).

1.15 equivalents of aminopyridine II were first suspended or dissolved in dichloromethane (2 ml per mmol of isonitrile IV used) in a reaction vessel. 1.5 equivalents of aldehyde III, 1 equivalent of tert-butyl isonitrile and finally aqueous perchloric acid solution (20% by weight; 0.098 ml per mmol isonitrile IV) were added thereto in succession and the batch was stirred for twenty hours at room temperature.

For work-up, saturated sodium chloride solution (about 5 ml per mmol isonitrile IV used) and dichloromethane (about 4 ml per mmol isonitrile IV used) were added, the phases were separated and the organic phase was extracted twice with dichloromethane (about 2 ml per mmol isonitrile IV used each time). The combined organic phases were was successively with buffer solution (pH 10: about 2 ml per mmol isonitrile IV used) and saturated sodium chloride solution (about 2 ml per mmol isonitrile IV used), dried over sodium sulphate, filtered, concentrated under vacuum in a rotary evaporator, and freed from residual solvents under an oil pump vacuum.

The crude product obtained was either fed directly to a hydrochloride precipitation stage (dissolution of the crude base in about 10 ml 2-butanone per gram of base; addition of 0.5 molar equivalents of water followed by 1.1 molar equivalents of chlorotrimethylsilane (TMSCl) and stirring overnight) or was heated with hexane (about 10 ml per mmol of isonitrile used) to reflux, with stirring. If the crude product did not dissolve completely, it was removed by hot decantation. After cooling the hexane solution, any solid obtained was filtered off and dried under an oil pump vacuum. The filtrate obtained was concentrated in a rotary evaporator and the residue was again dried under an oil pump vacuum. Different fractions were obtained in this manner:

0: no treatment with hexane
2: solid precipitated from hexane solution on cooling
4: residue from hexane solution which was concentrated for drying.

The product fractions from the fractions obtained were identified by thin layer chromatography and/or NMR spectroscopy. Finally, the hydrochloride was precipitated with TMSCl, by the method described above, from part of a product fraction.

Example compounds 18–20 which were obtained were tested for NOS inhibition by citrulline assay. The results are given in Table 3.

TABLE 3

| Example No. | Compound | Batch mmol isonitrile | Yield g product fraction | Product fraction(s) | Citrulline assay IC$_{50}$ (μM) |
|---|---|---|---|---|---|
| 18 | tert-butyl-(2-furan-2-yl-5,7-dimethyl-imidazo[1,2-a]pyridin-3-yl)amine hydrochloride | 18.8 | 4.64 | 0 | 2.8 |
| 19 | tert-butyl-(7-methyl-2-phenylimidazo[1,2-a]pyridin-3-yl)amine hydrochloride | 54.1 | 9.06 | 2 | 2.4 |
| 20 | tert-butyl-(2,5,7-trimethyl[1,2-a]pyridin-3-yl)amine hydrochloride | 48.1 | 10.5 | 2 and 4 | 9.2 |

As a comparison example, the NOS inhibitor 7-nitroindazole which is known from the prior art was tested by the citrulline assay, and gave an IC$_{50}$ value of 5.23 μM.

Pharmaceutical Formulation of a Drug According to the Invention 1 g of the hydrochloride of tert-butyl-(2-furan-2-yl-5,7-dimethyl-imidazo[1,2-a]pyridin-3-yl)-amine was dissolved in water at room temperature for injection purposes and was subsequently adjusted to isotonic conditions by adding sodium chloride.

The foregoing disclosure has been set forth merely to illustrate the invention and is not intended to be limiting. Since modifications of the disclosed embodiments incorporating the spirit and substance of the invention may occur to persons skilled in the art, the invention should be construed to broadly include everything within the scope of the appended claims and equivalents thereof.

What we claim:

1. A compound of Formula I

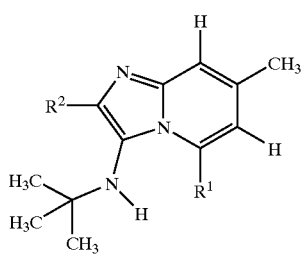

wherein
R$^1$ denotes, H or a C$_{1-4}$ alkanyl, wherein the alkanyl is straight-chain or branched and is unsubstituted or singly- or multiply-substituted, and
R$^2$ denotes an aryl, wherein the aryl is unsubstituted or singly or multiply-substituted, or a heteroaryl, wherein the heteroaryl is unsubstituted or singly or multiply-substituted,
wherein singly or multiply substituted denotes substitution by one or more substituents selected from the group consisting of F, Cl, Br, I, CN, NH$_2$, NH-alkyl, NH-aryl, NH-heteroaryl, NH alkyl-aryl, NH alkyl-heteroaryl, NH-heterocyclyl, NH-alkyl-OH, N(alkyl)$_2$, N(alkyl-aryl)$_2$, N(alkyl-heteroaryl)$_2$, N(heterocyclyl)$_2$, N(alkyl-OH)$_2$, or by NO, NO$_2$, SH, S-alkyl, S-aryl, S-heteroaryl, S-alkyl-aryl, S-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(=O)C$_{1-6}$-alkyl, C(=S)C$_{1-6}$-alkyl, C(=O)aryl, C(=S)aryl, C(=O)C$_{1-6}$- alkyl,

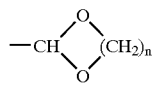

where n=1, 2 or 3, C(=S)C$_{1-6}$-alkyl, C(=S)C$_{1-6}$-alkyl-aryl, C(=O)-heteroaryl, C(=S)-heteroaryl, C(=O)heterocyclyl, C(=S)-heterocyclyl, CO$_2$H, CO$_2$-alkyl, CO$_2$-alkyl-aryl, C(=O)NH$_2$, C(=O)NH-alkyl, C(=O)N-aryl, C(=O)NH-heterocyclyl, C(=O)N(alkyl)$_2$, C(=O)N(alkyl-aryl)$_2$, C(=O)N(alkyl-heteroaryl), C(=O)N(heterocyclyl)$_2$, SO-alkyl, SO$_2$-alkyl, SO$_2$NH$_2$, SO—H, cycloalkyl, aryl, heteroaryl or heterocyclyl,
or a pharmaceutically acceptable salt thereof,
with the proviso that the compound of Formula I wherein R$^1$=methyl and R$^2$=phenyl is excluded.

2. A compound according to claim 1, wherein R$^1$ is H or methyl.

3. A compound of Formula I

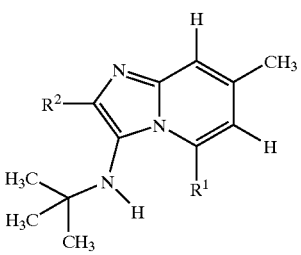

wherein
R$^1$ denotes H or a C$_{1-4}$ alkanyl, wherein the alkanyl is straight-chain or branched and is unsubstituted or singly- or multiply-substituted, and
R$^2$ is 1-naphthyl, phenyl, furyl, thienyl or pyridinyl, and is unsubstituted or singly- or multiply-substituted,
wherein singly or multiply substituted denotes substitution by one or more substituents selected from the group consisting of F, Cl, Br, I, CN, NH$_2$, NH-alkyl, NH-aryl, NH-heteroaryl, NH alkyl-aryl, NH alkyl-heteroaryl, NH-heterocyclyl, NH-alkyl-OH, N(alkyl)$_2$, N(alkyl-aryl)$_2$, N-(alkyl-heteroaryl)$_2$, N(heterocyclyl)$_2$, N(alkyl-OH)$_2$, or by NO, NO$_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(=O)C$_{1-6}$-alkyl, C(=S)C$_{1-6}$-alkyl, C(=O)aryl, C(=S)aryl, C(=O)C$_{1-6}$- alkyl,

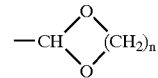

where n=1, 2 or 3, C(=S)C$_{1-6}$-alkyl, C(=S)C$_{1-6}$-alkyl-aryl, C(=O)-heteroaryl, C(=S)-heteroaryl, C(=O)heterocyclyl, C(=S)-heterocyclyl, CO$_2$H, CO$_2$-alkyl, CO$_2$-alkyl-aryl, C(=O)NH$_2$, C(=O)NH-alkyl, C(=O)N-aryl, C(=O)NH-heterocyclyl, C(=O)N(alkyl)$_2$, C(=O)N(alkyl-aryl)$_2$, C(=O)N(alkyl-heteroaryl), C(=O)N(heterocyclyl)$_2$, SO-alkyl, SO$_2$-alkyl, SO$_2$NH$_2$, SO—H, cycloalkyl, aryl, heteroaryl or heterocyclyl
or a pharmaceutically acceptable salt thereof,
with the proviso that the compound of Formula I wherein R$^1$=methyl and R$^2$=phenyl is excluded.

4. A compound according to claim 3, wherein R$^1$ is H or methyl.

5. A hydrochloride salt of a compound according to claim 1.

6. A compound selected from the group consisting of:
tert.-butyl-(7-methyl-2-pyridin-3-yl-imidazo[1,2-a]pyridin-3-yl)-amine,
tert.-butyl-[2-(2,3-dimethoxy-phenyl)-5,7-dimethyl-imidazo[1,2-a]pyridin-3-yl]-amine,
tert-butyl-(2,5,7-tri-methyl-imidazo[1,2-a]pyridin-3-yl)-amine,
3-(3-tert.-butylamino-5,7-dimethyl-imidazo[1,2-a]pyridin-2-yl)-phenol,
tert.-butyl-(2-cyclohexyl-5,7-dimethyl-imidazo[1,2-a]pyridin-3-yl)-amine,
3-(3-tert.-butylamino-7-methyl-imidazo[1,2-a]pyridin-2-yl)-phenol, tert.-butyl-(2-furan-2-yl-5,7-dimethyl-imidazo[1,2-a]pyridin-3-yl)-amine, tert.-butyl-(7-methyl-2-naphthalen-1-yl-imidazo[1,2-a]pyridin-3-yl) amine, tert.-butyl-(5,7-dimethyl-2-(5-nitro-furan-2-yl)-imidazo[1,2-a]pyridin-8-yl]-amine,

[5-(3-tert.-butylamino-7-methyl-imidazo[1,2-a]pyridin-2-yl)-furan-2-yl]-methanol, tert.-butyl-[2-(5-[1,3]dioxolan-2-yl-furan-2-yl)-7-methyl-imidazo[1,2-a]-pyridin-3-yl]-amine,

[5-(3-tert.-butylamino-5,7-dimethyl-imidazo[1,2-a]pyridin-2-yl)-furan-2-carboxylic acid, tert.-butyl-(2-furan-2-yl-7-methyl-imidazo[1,2-a]pyridin-3-yl)-amine, tert.-butyl-(7-methyl-2-pyridin-2-yl-imidazo[1,2-a]pyridin-3-yl)-amine, tert.-butyl-(2-cyclohexyl-7-methyl-imidazo[1,2-a]pyridin-3-yl)-amine, tert.-butyl-(2,7-dimethyl-imidazo[1,2-a]pyridin-3-yl)-amine, 5-(3-tert.-butylamino-7-methyl-imidazo[1,2-a]pyridin-2-yl)-thiophen-2-carboxylic acid, tert.-butyl-(7-methyl-2-phenyl-imidazo[1,2-a]pyridin-3-yl)-amine, and pharmaceutically acceptable salts thereof.

7. A method for producing a compound according to claim 1, the method comprising:

reacting an aminopyridine of Formula II

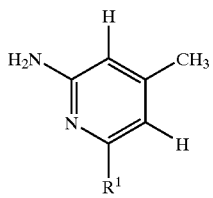

wherein $R^1$ is H or a $C_{1-4}$ alkanyl, wherein the alkanyl is straight-chain or branched and is unsubstituted or singly- or multiply-substituted, with an aldehyde of Formula III

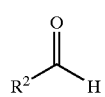

wherein $R^2$ denotes an aryl, wherein the aryl is unsubstituted or singly or multiply-substituted, or a heteroaryl, wherein the heteroaryl is unsubstituted or singly or multiply-substituted, with the proviso that $R^2$ is not phenyl if $R^1$ is methyl, and with tert.-butyl isonitrile of Formula IV

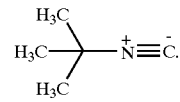

8. A method according to claim 7, wherein the aminopyridine, the aldehyde and the tert.-butyl isonitrile are reacted in the presence of an acid.

9. A method according to claim 8, wherein the acid is perchloric acid.

10. A method according to claim 7, wherein the aminopyridine of Formula II, the aldehyde of Formula III and tert.-butyl isonitrile of Formula IV are reacted in a one-pot process.

11. A method according to claim 7, further comprising converting a base of Formula I into a hydrochloride salt by an addition of trimethylchlorosilane.

12. A pharmaceutical composition comprising at least one compound of Formula I:

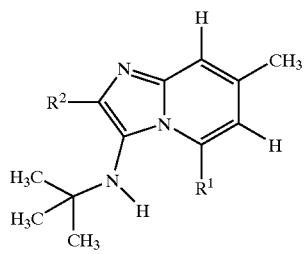

wherein $R^1$ denotes H or a $C_{1-4}$ alkanyl, wherein the alkanyl is straight-chain or branched and is unsubstituted or singly- or multiply-substituted, and $R^2$ denotes an aryl, wherein the aryl is unsubstituted or singly or multiply-substituted, or a heteroaryl, wherein the heteroaryl is unsubstituted or singly or multiply-substituted, wherein singly or multiply substituted denotes substitution by one or more substituents selected from the group consisting of F, Cl, Br, I, CN, $NH_2$, NH alkyl, NH-aryl, NH-heteroaryl, NH-alkyl-aryl, NH-alkyl-heteroaryl, NH-heterocyclyl, NH-alkyl-OH, N(alkyl)$_2$, N-(alkyl-aryl)$_2$, N(alkyl-heteroaryl)$_2$, N(heterocyclyl)$_2$, N(alkyl-OH)$_2$, or by NO, $NO_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$- alkyl,

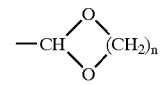

where n=1, 2 or 3, C(=S)$C_{1-6}$-alkyl, C(=S)$C_{1-6}$-alkyl-aryl, C(=O)-heteroaryl, C(=S)-heteroaryl, C(=O)heterocyclyl, C(=S)-heterocyclyl, $CO_2H$, $CO_2$-alkyl, $CO_2$-alkyl-aryl, C(=O)$NH_2$, C(=O)NH-alkyl, C(=O)N-aryl, C(=O)NH-heterocyclyl, C(=O)N(alkyl)$_2$, C(=O)N(alkyl-aryl)$_2$, C(=O)N(alkyl-heteroaryl), C(=O)N(heterocyclyl)$_2$, SO-alkyl, SO$_2$-alkyl, SO$_2$NH$_2$, SO—H, cycloalkyl, aryl, heteroaryl or heterocyclyl or a pharmaceutically acceptable salt thereof, and a pharmaceutically acceptable excipient.

13. A method of inhibiting NO synthase in a subject, comprising administering to said subject an effective NO synthase-inhibiting amount of a compound of Formula I

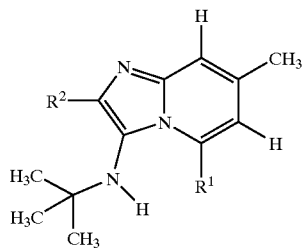

wherein

R$^1$ denotes H or a C$_{1-4}$ alkanyl, wherein the alkanyl is straight-chain or branched and is unsubstituted or singly- or multiply-substituted, and R$^2$ denotes an aryl, wherein the aryl is unsubstituted or singly or multiply-substituted, or a heteroaryl, wherein the heteroaryl is unsubstituted or singly or multiply-substituted, wherein singly or multiply substituted denotes substitution by one or more substituents selected from the group consisting of F, Cl, Br, I, CN, NH$_2$, NH alkyl, NH-aryl, NH-heteroaryl, NH-alkyl-aryl, NH-alkyl-heteroaryl, NH-heterocyclyl, NH-alkyl-OH, N(alkyl)$_2$, N-(alkyl-aryl)$_2$, N(alkyl-heteroaryl)$_2$, N(heterocyclyl)$_2$, N(alkyl-OH)$_2$, or by NO, NO$_2$, SH, S-alkyl, S-aryl, S-heteroaryl, S-alkyl-aryl, S-alkyl-heteroaryl, S-heterocyclyl, S-alkyl-OH, S-alkyl-SH, OH, O-alkyl, O-aryl, O-heteroaryl, O-alkyl-aryl, O-alkyl-heteroaryl, O-heterocyclyl, O-alkyl-OH, CHO, C(=O)C$_{1-6}$-alkyl, C(=S)C$_{1-6}$-alkyl, C(=O)aryl, C(=S)aryl, C(=O)C$_{1-6}$- alkyl,

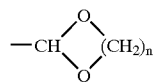

where n=1, 2 or 3, C(=S)C$_{1-6}$-alkyl, C(=S)C$_{1-6}$-alkyl-aryl, C(=O)-heteroaryl, C(=S)-heteroaryl, C(=O)heterocyclyl, C(=S)-heterocyclyl, CO$_2$H, CO$_2$-alkyl, CO$_2$-alkyl-aryl, C(=O)NH$_2$, C(=O)NH-alkyl, C(=O)N-aryl, C(=O)NH-heterocyclyl, C(=O)N(alkyl)$_2$, C(=O)N(alkyl-aryl)$_2$, C(=O)N(alkyl-heteroaryl), C(=O)N(heterocyclyl)$_2$, SO-alkyl, SO$_2$-alkyl, SO$_2$NH$_2$, SO—H, cycloalkyl, aryl, heteroaryl or heterocyclyl or a pharmaceutically acceptable salt thereof.

14. A method of inhibiting NO synthase in a subject, comprising administering to said subject an effective NO synthase-inhibiting amount of a compound selected from the group consisting of tert.-butyl-(7-methyl-2-pyridin-3-yl-imidazo[1,2-a]pyridin-3-yl)-amine, tert.-butyl-[2-(2,3-dimethoxy-phenyl)-5,7-dimethyl-imidazo[1,2-a]pyridin-3-yl]-amine, tert-butyl-(2,5,7-tri-methyl-imidazo[1,2-a]pyridin-3-yl)-amine, 3-(3-tert.-butylamino-5,7-dimethyl-imidazo[1,2-a]pyridin-2-yl)-phenol, tert.-butyl-(2-cyclohexyl-5,7-dimethyl-imidazo[1,2-a]pyridin-3-yl)-amine, 3-(3-tert.-butylamino-7-methyl-imidazo[1,2-a]pyridin-2-yl)-phenol, tert.-butyl-(2-furan-2-yl-5,7-dimethyl-imidazo[1,2-a]pyridin-3-yl)-amine, tert.-butyl-(7-methyl-2-naphthalen-1-yl-imidazo[1,2-a]pyridin-3-yl)amine, tert.-butyl-(5,7-dimethyl-2-(5-nitro-furan-2-yl)-imidazo[1,2-a]pyridin-3-yl]-amine,

[5-(3-tert.-butylamino-7-methyl-imidazo[1,2-a]pyridin-2-yl)-furan-2-yl]-methanol, tert.-butyl-[2-(5-[1,3]dioxolan-2-yl-furan-2-yl)-7-methyl-imidazo[1,2-a]-pyridin-3-yl]-amine,

[5-(3-tert.-butylamino-5,7-dimethyl-imidazo[1,2-a]pyridin-2-yl)-furan-2-carboxylic acid, tert.-butyl-(2-furan-2-yl-7-methyl-imidazo[1,2-a]pyridin-3-yl)-amine, tert.-butyl-(7-methyl-2-pyridin-2-yl-imidazo[1,2-a]pyridin-3-yl)-amine, tert.-butyl-(2-cyclohexyl-7-methyl-imidazo[1,2-a]pyridin-3-yl)-amine, tert.-butyl-(2,7-dimethyl-imidazo[1,2-a]pyridin-3-yl)-amine, 5-(8-tert.-butylamino-7-methyl-imidazo[1,2-a]pyridin-2-yl)-thiophen-2-carboxylic acid, tert.-butyl-(7-methyl-2-phenyl-imidazo[1,2-a]pyridin-3-yl)-amine, and pharmaceutically acceptable salts thereof.

15. The method according to claim 13, wherein the subject is a mammal.

16. The method according to claim 15, wherein the mammal is a human.

17. A method for the treatment of migraine, septic shock, multiple sclerosis, Parkinson's disease, Alzheimer's disease, Huntington's disease, inflammation, pain due to inflammation, cerebral ischaemia, diabetes, meningitis, arteriosclerosis or for the healing of wounds, comprising administering an effective amount for NO synthase inhibition of a pharmaceutical composition according to claim 16 to a patient in need thereof.

18. A compound according to claim 3, wherein the 1-naphthyl, phenyl, furyl, thienyl or pyridinyl is unsubstituted or is singly- or doubly-substituted with —F, —CF$_3$, —OCH$_3$, —CH$_2$OH, —NO$_2$, —CO$_2$H or -[1,3]-dioxolane.

19. A compound according to claim 18, wherein the 1-naphthyl, phenyl, furyl, thienyl or pyridinyl is unsubstituted or is singly- or doubly-substituted with —F, —CF$_3$, —OCH$_3$, —CH$_2$OH, —NO$_2$, —CO$_2$H or -[1,3]-dioxolane.

20. A pharmaceutical composition comprising at least one compound selected from the group consisting of:

tert.-butyl-(7-methyl-2-pyridin-3-yl-imidazo[1,2-a]pyridin-3-yl)-amine, tert.-butyl-[2-(2,3-dimethoxy-phenyl)-5,7-dimethyl-imidazo[1,2-a]pyridin-3-yl]-amine, tert-butyl-(2,5,7-tri-methyl-imidazo[1,2-a]pyridin-3-yl)-amine, 3-(3-tert.-butylamino-5,7-dimethyl-imidazo[1,2-a]pyridin-2-yl)-phenol, tert.-butyl-(2-cyclohexyl-5,7-dimethyl-imidazo[1,2-a]pyridin-3-yl)-amine, 3-(3-tert. -butylamino-7-methyl-imidazo[1,2-a]pyridin-2-yl)-phenol, tert.-butyl-(2-furan-2-yl-5,7-dimethyl-imidazo[1,2-a]pyridin-3-yl)-amine, tert.-butyl-(7-methyl-2-naphthalen-1-yl-imidazo[1,2-a]pyridin-3-yl) amine, tert.-butyl-(5,7-dimethyl-2-(5-nitro-furan-2-yl)-imidazo[1,2-a]pyridin-3-yl]-amine,

[5-(3-tert.-butylamino-7-methyl-imidazo[1,2-a]pyridin-2-yl)-furan-2-yl]-methanol, tert.-butyl-[2-(5-[1,3]dioxolan-2-yl-furan-2-yl)-7-methyl-imidazo[1,2-a]-pyridin-3-yl]-amine,

[5-(3-tert.-butylamino-5,7-dimethyl-imidazo[1,2-a]pyridin-2-yl)-furan-2-carboxylic acid, tert.-butyl-(2-furan-2-yl-7-methyl-imidazo[1,2-a]pyridin-3-yl)-amine, tert.-butyl-(7-methyl-2-pyridin-2-yl-imidazo[1,2-a]pyridin-3-yl)-amine, tert.-butyl-(2-cyclohexyl-7-methyl-imidazo[1,2-a]pyridin-3-yl)-amine, tert.-butyl-(2,7-dimethyl-imidazo[1,2-a]pyridin-3-yl)-amine, 5-(3-tert.-butylamino-7-methyl-imidazo[1,2-a]pyridin-2-yl)-thiophen-2-carboxylic acid, tert. -butyl-(7-methyl-2-phenyl-imidazo[1,2-a]pyridin-3-yl)-amine, and pharmaceutically acceptable salts thereof, and a pharmaceutically acceptable excipient.

21. The method according to claim 14, wherein the subject is a mammal.

* * * * *